United States Patent [19]

Heitmann et al.

[11] Patent Number: 4,645,921
[45] Date of Patent: Feb. 24, 1987

[54] APPARATUS FOR TESTING ROD-SHAPED PRODUCTS OF THE TOBACCO PROCESSING INDUSTRY

[75] Inventors: Uwe Heitmann, Hamburg; Peter Pinck, Gross-Hansdorf; Elke Köhler, Hamburg; Berthold Maiwald, Schwarzenbek; Uwe Marsau, Dassendorf, all of Fed. Rep. of Germany

[73] Assignee: Hauni-Werke Körber & Co. KG., Hamburg, Fed. Rep. of Germany

[21] Appl. No.: 665,129

[22] Filed: Oct. 26, 1984

[30] Foreign Application Priority Data

Oct. 28, 1983 [DE] Fed. Rep. of Germany ....... 3339187

[51] Int. Cl.⁴ .................. G01N 9/04; G06M 7/00; H01J 40/14
[52] U.S. Cl. .................. 250/223 R; 209/536
[58] Field of Search .............. 209/536; 250/223 R, 250/227, 572

[56] References Cited

U.S. PATENT DOCUMENTS

| | | | |
|---|---|---|---|
| 3,746,575 | 7/1973 | Arnaudin et al. | 250/572 |
| 4,025,770 | 5/1977 | Reuland | 250/223 R |
| 4,147,173 | 4/1979 | Reuland | 250/223 R |
| 4,162,126 | 7/1979 | Nakagawa et al. | 250/572 |
| 4,208,578 | 6/1980 | McLoughlin et al. | 209/536 |
| 4,212,541 | 7/1980 | Ducomman et al. | 250/572 |
| 4,249,081 | 2/1981 | Cole et al. | 250/572 |
| 4,377,743 | 3/1983 | Bolt et al. | 209/536 |

FOREIGN PATENT DOCUMENTS 0472280 2/1929 Fed. Rep. of Germany ...... 209/536

Primary Examiner—Edward P. Westin
Assistant Examiner—William L. Oen
Attorney, Agent, or Firm—Peter K. Kontler

[57] ABSTRACT

Apparatus for optically scanning a moving cigarette rod for the presence of defects in its external surface has two annularly arranged groups of diodes which emit green light in the wavelength range of between 0.49 and 0.58$\mu$ and direct such light from the opposite sides of a plane that is normal to the moving rod so that the incident light is reflected by successive annular portions of the external surface of the rod into the aforementioned plane. The reflected light is focused by systems of lenses upon discrete photosensitive transducers through discrete slit diaphragms on the transducers themselves or on a thin metallic ring which is adjustably mounted on the support for the diodes and the systems of lenses.

22 Claims, 3 Drawing Figures

APPARATUS FOR TESTING ROD-SHAPED PRODUCTS OF THE TOBACCO PROCESSING INDUSTRY

BACKGROUND OF THE INVENTION

The present invention relates to improvements in apparatus for optically testing or scanning rod-shaped commodities, and more particularly to improvements in apparatus for testing rod-shaped materials of the tobacco processing industry. Typical examples of rod-shaped materials which can be tested in such apparatus are continuous cigarette rods or filter rods or files or rows of discrete plain or filter cigarettes, filter rod sections or the like.

It is already known to equip an apparatus for optical testing of cigarette rods or the like with an annular support which surrounds a portion of the course or path for the moving rod and carries an annulus of light sources serving to direct infrared light upon successive increments of the external surface of the rod. The reflected light is directed upon an annulus of photosensitive detectors which transmit defect signals when the intensity of reflected light is changed as a result of the presence of a defect (such as a hole in the wrapper or a spot of adhesive). The signals are transmitted to an evaluating circuit which records the number of defects and/or generates signals for segregation of corresponding cigarettes from satisfactory cigarettes. The just outlined conventional apparatus can be used to detect defects in the form of holes in or smudges on the tubular wrapper of a cigarette rod or filter rod, the absence of improper application of imprints denoting the trademark, the trade name or other information pertaining to the manufacturer and/or to the product and spots of adhesive outside of the customary seam between the overlapping marginal portions of the wrapper. Spots of adhesive normally reflect more light than cigarette paper so that they effect an intensification of signals which are generated by the respective detector or detectors. On the other hand, holes in the wrapper consisting of cigarette paper or the like act not unlike dark spots and reduce the intensity of reflected light. Imprints influence the reflection of light to an extent which depends upon their color tone. Thus, the evaluating circuit which receives signals from the detectors can classify the incoming signals according to their intensity and hence according to the types of defects.

German Offenlegungsschrift No. 29 40 408 discloses a testing apparatus wherein light issuing from a source passes through a ring-shaped light-transmitting prism at an oblique angle to a plane which is normal to the axis of the tested rod-shaped material. Reflected light is intercepted by a set of light conducting elements in the form of glass fibers and is conducted to an optoelectrical transducer which generates signals whose intensity is proportional to the intensity of reflected light. Signals which are transmitted by the output of the transducer can be used to regulate the operation of the machine and/or to effect segregation of defective articles. The provision of a light source which directs light at an oblique angle with reference to the aforementioned plane is considered desirable and advantageous because it increases the contrasts which are attributable to irregularities in the region of defects, i.e., such orientation of incident light enhances the sensitivity of the testing apparatus. However, the just described testing apparatus also exhibits certain serious drawbacks which are attributable to the aforementioned orientation of incident light. Thus, light which impinges upon successive increments of the external surface of the moving rod-shaped material creates pronounced shadows whenever it encounters unevennesses in the external surface irrespective of whether or not such unevennesses are attributable to the presence of defects. The thus developing pronounced shadows are detected by the photosensitive transducer means and the latter transmits signals which lead to the segregation of the corresponding articles even though such articles are not defective at all. For example, slight undulations and/or minute creases in the wrapper of a cigarette rod are likely to induce the transducer means to generate defect signals even though the corresponding portion of the moving rod is not defective in a sense which would be irritating to the purchaser of cigarettes.

Another drawback of presently known testing apparatus is that they cannot detect all such defects which are detectable by the human eye and are likely to be irritating or unacceptable to the consumer. For example, a testing apparatus which operates with red or infrared light (such light is presently used in numerous testing apparatus for cigarettes or the like) cannot detect specks or smudges of oil or other fatty substances even though a purchaser will detect such defects and they are likely to deter him or her from making further purchases of the same brand.

OBJECTS AND SUMMARY OF THE INVENTION

An object of the invention is to provide a novel and improved apparatus for optically testing rodshaped materials of the tobacco processing industry with a higher degree of accuracy, reliability and predictability than heretofore known testing apparatus.

Another object of the invention is to provide a testing apparatus which is surprisingly compact and is more versatile than the aforedescribed and other conventional apparatus.

A further object of the invention is to provide a testing apparatus whose testing action more accurately resembles visual testing by a purchaser of smokers' articles than the testing action of prior apparatus.

An additional object of the invention is to provide a testing apparatus which is less likely to initiate the ejection or segregation of acceptable products than heretofore known apparatus.

Still another object of the invention is to provide a testing apparatus which can detect smudges or spots of oil or like defects with the same degree of reliability as a wide variety of other types of defects, such as holes in the wrapper, frayed ends of discrete articles, open seams of the wrappers, absence of imprints, improperly applied imprints, spots of adhesive, absence of filter mouthpieces in filter cigarettes and many others.

A further object of the invention is to provide novel and improved light sources and photosensitive detector means for use in apparatus for the testing of rod-shaped materials of the tobacco processing industry.

Another object of the invention is to provide a novel and improved method of testing rod-shaped materials of the tobacco processing industry with one or more light sources which render it possible to increase the versatility and reliability of the testing action without the generation of false signals which could lead to segregation of satisfactory smokers' products.

An additional object of the invention is to provide a testing apparatus which can be used as a superior substitute for heretofore known apparatus in connection with the testing of continuous or discrete rod-shaped products of the tobacco processing industry.

One feature of the invention resides in the provision of an apparatus for scanning the external surface of a moving rod-shaped product of the tobacco processing industry for the presence or absence of smaller or larger defects (such as open seams, smudges, holes, spots of adhesive, improperly applied imprints, absence of imprints and/or others), especially for scanning the external surfaces of a series of coaxial discrete or coherent cigarettes. The apparatus comprises guide means defining a predetermined elongated course or path along which the product to be tested moves axially, a support surrounding a portion of the course, illuminating means including at least one ring-shaped group of light emitting devices which are carried by the support and serve to direct light (preferably green light) against the external surfaces of successive increments of the product so that such external surfaces reflect light into a predetermined plane, an annulus of diaphragms which spacedly surround the course and are disposed in the path of propagation of light which is reflected light into the plane, and a light-sensitive detector disposed immediately behind each diaphragm, as considered in the direction of propagation of reflected light. The aforementioned plane is or can be at least substantially normal to the course for the product and the illuminating means preferably comprises two groups of light emitting devices. The two groups are then disposed at the opposite sides of the aforementioned plane and the light emitting devices in each of the two groups are arranged to direct light at an oblique angle to the course and into the region where the plane intersects the course. Each diaphragm is preferably a slit diaphragm and all of the diaphragms can be defined by a substantially ring-shaped carrier which is mounted on the support and carries the detectors each of which can constitute a photosensitive transducer. Each slit-shaped diaphragm preferably extends in the circumferential direction of the carrier and the diaphragms are preferably equidistant from each other, as considered in the circumferential direction of their carrier.

The apparatus preferably further comprises means for focusing reflected light upon the diaphragms. The external surfaces of successive increments of the product in the elongated course are normally circumferentially complete annular surfaces, and the focusing means preferably comprises optical elements (e.g., each such optical element can comprise a set of lenses) each of which serves to focus light which is reflected by arcuate sections of annular surfaces of successive increments of the product. In accordance with a presently preferred embodiment, each arcuate section has a substantially rectangular outline and the ratio of the areas of such arcuate sections to the areas of slits in the respective diaphragms preferably equals or approximates two-to-one. The width of the aforementioned annular surfaces, as considered in the longitudinal direction of the course for the product, preferably equals or approximates the maximum dimension of the smallest defect (e.g., a spot of adhesive or a hole) which is to be detected by the apparatus.

The distribution of optical elements of the focusing means around the course for the product is preferably such that the neighboring arcuate sections overlap each other, as considered in the circumferential direction of the carrier for diaphragms. The extent of overlap of neighboring arcuate sections preferably equals or approximates the maximum dimension of the smallest defect which is to be detected by the apparatus.

In accordance with a presently preferred embodiment of the invention, each light emitting device is arranged to emit light in the wavelength range of between 0.5 and 0.7 $\mu$, most preferably between 0.49 and 0.58 $\mu$.

The detectors can be adhesively secured to the carrier for diaphragms, and such carrier can consist of several pieces which are assembled into a ring. The ring can constitute a metallic band having a series of circumferentially extending slits each of which constitutes a discrete diaphragm and is located in front of a detector. The optical elements of the focusing means preferably include a system of lenses of great focal length for each of the diaphragms.

In accordance with a modification, the aforementioned ring-shaped carrier can support an annulus of detectors, e.g., photoelectric transducers, each of which has a light-sensitive surface and a coating or layer of opaque material which is applied to the respective light-sensitive surface and constitutes the corresponding diaphragm. Each such coating or layer defines a slit for the passage of reflected light to the respective light-sensitive surface.

Another feature of the invention resides in the provision of an apparatus for scanning the external surface of a moving rod-shaped product of the tobacco processing industry for the presence or absence of defects, especially for scanning the external surfaces of a series of coherent or discrete coaxial cigarettes, filter rod sections or the like. The apparatus comprises means for illuminating successive increments of the external surface of the moving product so that such increments reflect incident light. The illuminating means is arranged to emit green light in the wavelength range of between 0.49 and 0.58 $\mu$, and the apparatus further comprises detector means, e.g., photoelectric transducer means, disposed in the path of propagation of light which is reflected by successive increments and being sensitive to light in the aforementioned range of wavelengths. The illuminating means preferably comprises a plurality of green light emitting diodes.

The novel features which are considered as characteristic of the invention are set forth in particular in the appended claims. The improved testing apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
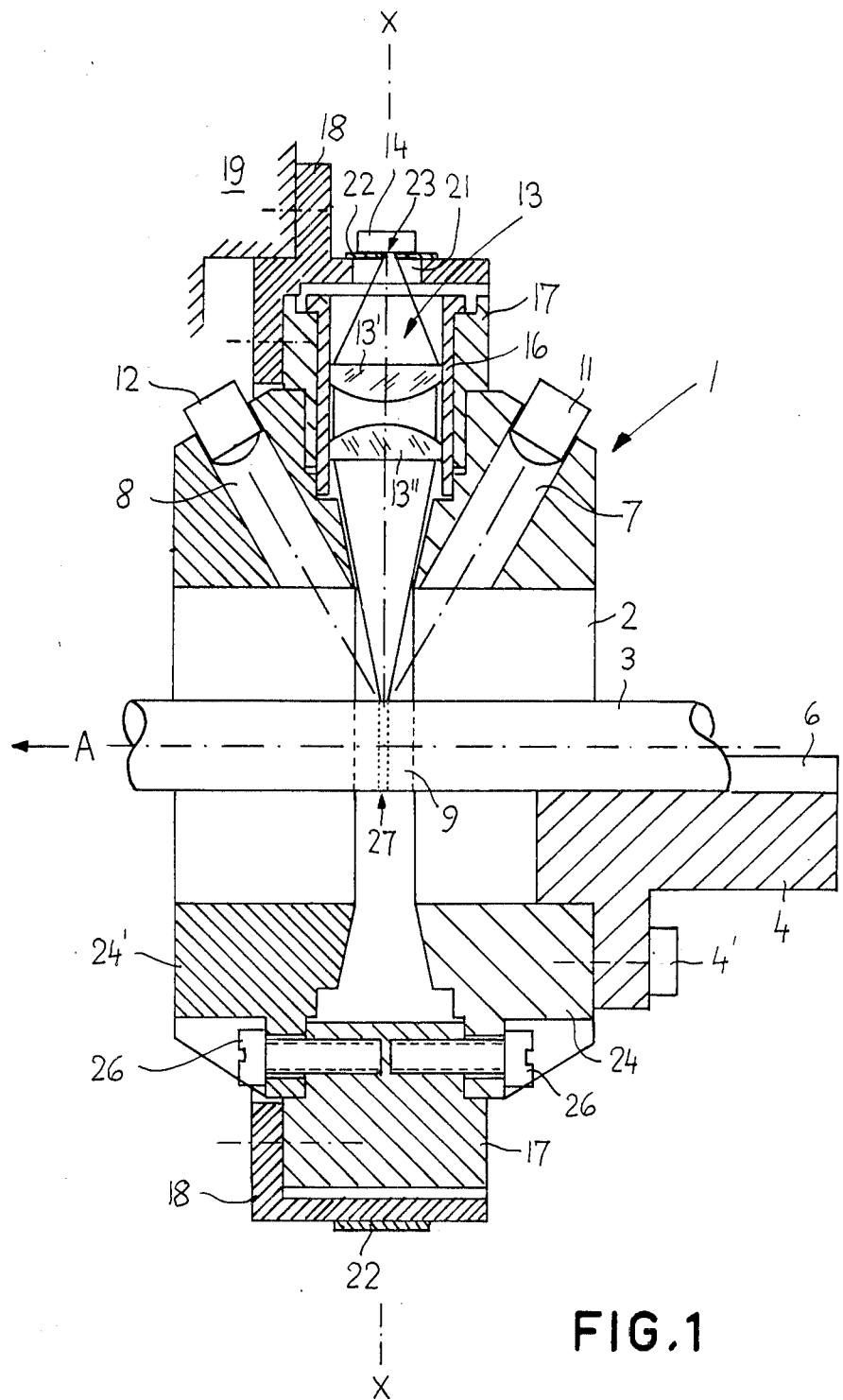
FIG. 1 is a sectional view of a testing apparatus which embodies one form of the invention, the section being taken in the direction of arrows as seen from the line I—I of FIG. 2.
Figure 2:
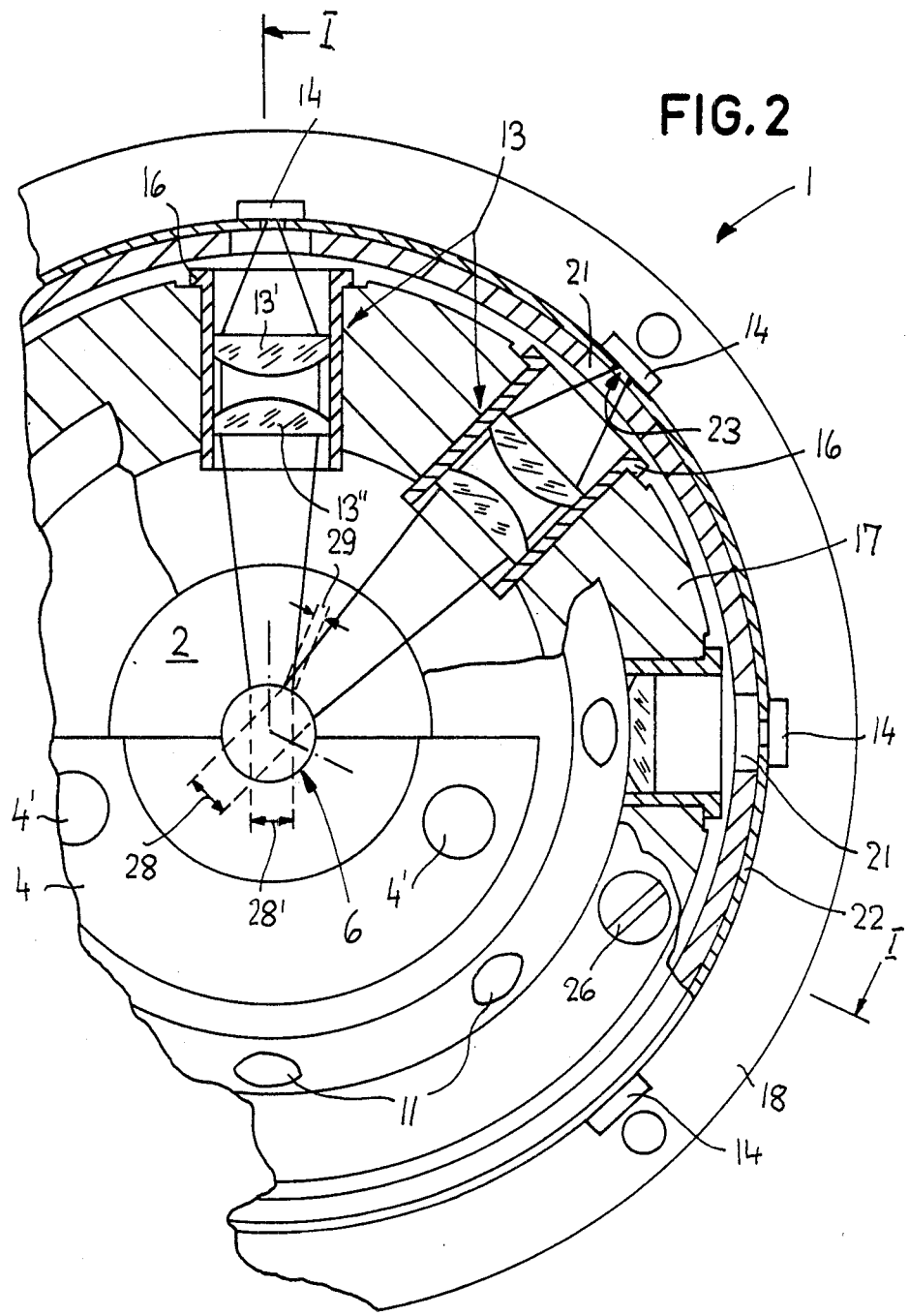
FIG. 2 is a fragmentary partly end elevational and partly transverse vertical sectional view of the testing apparatus which is shown in FIG. 1.

The testing apparatus of FIGS. 1 and 2 is designed to scan the external surface of a moving rod-shaped product 3 of the tobacco processing industry. The illustrated product 3 is a continuous cigarette rod which is turned out in a cigarette making machine and moves lengthwise (axially) along a predetermined (preferably but not necessarily horizontal) course or path defined by one or more guides 4. The illustrated guide 4 has an elongated flute or groove 6 which is bounded by a semicircular surface and receives a portion of the moving rod 3 which is assumed to move in a direction to the left, as viewed in FIG. 1 (note the arrow A). The guide 4 extends in part into the central opening 2 of a stationary ring-shaped support 1 and is secured to the support by a set of screws 4' or other suitable fastener means. In order to further enhance the degree of accuracy with which the rod 3 is guided on its way through the opening 2 of the support 1, the latter can carry one or more additional guides. For example, a second guide 4 can be mounted at the left-hand side of the support 1 so that its flute 6 is open from below and guides the upper half of the external surface of the rod 3.

The support 1 is formed with two annuli of holes or bores 7 and 8 which are disposed at the opposite sides of a plane X—X. The latter is normal to the axis of the rod 3 in its course and intersects the course for the rod 3 in the centrally located opening 2 of the support 1. The axes of the holes 7 and 8 make oblique angles with the axis of the rod 3, i.e., with the course for the rod, and such axes intersect each other in the region where the plane X—X intersects the external surface of the rod 3 in the opening 2. The holes 7 are equidistant from each other, as considered in the circumferential direction of the rod 3, the same as the holes 8. The reference character 9 denotes the actual testing zone or station in the interior of the support 1. Such zone is halved by the plane X—X which is located midway between the annuli of holes 7 and 8. The purpose of the holes 7 and 8 is to receive the light emitting devices 11 and 12 of an illuminating means for the external surface of the rod 3. The arrangement is such that light issuing from the devices 11 and 12 illuminates the testing zone 9 and particularly a relatively narrow circumferentially complete annular surface 27 of that increment of the rod 3 which happens to be located in and immediately adjacent to the plane X—X. The annular surfaces 27 of successive increments of the moving rod 3 reflect the incident light and, in view of the aforedescribed inclination of holes 7 and 8, maximum reflection of incident light by successive annular surfaces 27 is expected to be in the plane X—X. The region of maximum intensity of reflected light is surrounded by focusing means which is installed in the support 1 and includes several sets or systems 13 of optical elements here shown as pairs of lenses 13' and 13". The sets 13 of optical elements 13', 13" are equidistant from each other, as considered in the circumferential direction of the rod portion in the testing zone 9, and each system 13 focuses reflected light upon a discrete light-sensitive detector in the form of a photoelectric transducer 14. The lenses 13', 13" of each system 13 are installed in a discrete sleeve 16 whose axis is disposed radially of the rod 3 and which is installed in the support 1 between the two groups of holes 7 and 8. The sleeves 16 are inserted into the radially extending bores of a ring-shaped holder 17 which is secured to the frame 19 of the cigarette rod making machine by means of a ring-shaped adapter 18. The latter has a cylindrical portion which surrounds the holder 17 for the sleeves 16 and has an annulus of apertures 21 each of which is in register with a discrete transducer 14 so that the systems 13 of the focusing means can focus reflected light upon the photosensitive surfaces of the respective transducers. The cylindrical portion of the adapter 18 is further surrounded by a ring-shaped carrier 22 which is a thin metallic band and is preferably assembled of several arcuate pieces and directly supports the transducers 14. The carrier 22 has an annulus of equidistant slit diaphragms 23 which extend in the circumferential direction of the support 1 and each of which registers with the respective aperture 21 of the adapter 18 so as to allow a certain amount of reflected light to reach the photosensitive surface of the respective transducer 14. Each transducer 14 is preferably bonded (e.g., adhesively secured) to the outer side of the carrier 22 immediately behind the respective diaphragm 23, as considered in the direction of propagation of light which is reflected by successive annular surfaces 27 of the rod 3. The optical axis of each system 13 of lenses 13', 13" passes through the corresponding aperture 21 and diaphragm 23.

The support 1 is preferably made of several parts for the convenience of assembly and dismantling. In the embodiment of FIGS. 1 and 2, the support 1 consists of two identical sections 24 and 24' which are mirror symmetrical to each other and are held in the positions shown in FIG. 1 by screws 26 which mesh with the holder 17. The section 24 is formed with the holes 7 for the light emitting devices 11, and the section 24' is formed with the holes 8 for the light emitting devices 12.

The light emitting devices 11 and 12 are preferably designed to emit visible light in the wavelength range of between 0.5 and 0.7 $\mu$, most preferably between 0.49 and 0.58 $\mu$. As mentioned above, the orientation of the light emitting devices 11 and 12 is such that they direct light primarily or exclusively into the testing zone 9, and especially against successive annular surfaces 27 of the moving rod 3. The focusing means including the systems 13 image the annular surfaces 27 upon the diaphragms 23 of the carrier 22. The width of the annular surfaces 27, as considered in the axial direction of the rod 3 (i.e., in the longitudinal direction of the course for the rod), preferably equals or approximates the maximum dimension of the smallest defect (e.g., a hole in or a smudge on the external surface of the rod 3) which is to be detected by the testing or scanning apparatus. For example, the axial length of each annular surface 27 can be in the range of one millimeter. Furthermore, the imaging ratio of the focusing means is preferably two-to-one, i.e., the length of each slit diaphragm 23, as considered in the circumferential direction of the carrier 22, is 0.5 mm if the axial length of the annular surface 27 is 1 mm.

As can be seen in FIG. 2, neighboring optical systems 13 of the focusing means focus light which is reflected from neighboring arcuate sections 28, 28' of successive annular surfaces 27 of the moving rod 3. Each of the arcuate sections 28, 28' is preferably a rectangle and its area is preferably twice the area of a diaphragm 23. In order to ensure that the transducers 14 will receive signals which invariably represent the characteristics of the entire annular surface 27 during each and every stage of testing of the quality of the external surface of the rod 3, the neighboring arcuate sections 28, 28' preferably partially overlap each other, as considered in the circumferential direction of the rod 3. The region of overlap is shown in FIG. 2, as at 29, and the extent of overlap preferably matches or approximates the maximum dimension of the smallest defect which is to be detected by the apparatus. For example, the extent of overlap of neighboring arcuate sections 28, 28' of the annular surface 27 at the center of the testing zone 9 can be in the range of 1 mm. In other words, not only the axial length of each annular surface 27 but also the extent of overlap between two neighboring arcuate sections 28, 28' of each annular surface 27 is selected in dependency on the desired resolution capability of the testing apparatus.

The provision of focusing means which ensures that the neighboring sections 28, 28' partially overlap each other is desirable and advantageous because it contributes to greater reliability and higher sensitivity of the improved testing apparatus. Thus, if a very small defect (whose maximum dimension does not exceed 1 mm) happens to be located, in its entirety, in a region 29 of overlap between two neighboring sections 28 and 28', the entire defect is fully detected by two transducers 14 which then transmit appropriate defect signals to the evaluating circuit of the testing apparatus. If the defect is shifted in the circumferential direction of the carrier 22 so that the major or the minor part of such defect is located in the non-overlapping part of one of the sections 28, 28' and the remaining part of the defect is located in the region 29 of overlap, the defect is fully registered by one of the transducers 14 so that the evaluating circuit again receives a defect signal which is indicative of a defect that warrants segregation of the corresponding cigarette from satisfactory cigarettes. In the absence of regions 29 of overlap between neighboring sections 28 and 28' of successive annular surfaces 27, a small defect which would be located at the boundary between two abutting (rather than overlapping) sections 28, 28' would cause two neighboring transducers 14 to generate relatively weak signals which would not induce the evaluating circuit to effect segregation of the corresponding cigarette from satisfactory cigarettes. Thus, the provision of the aforementioned regions 29 of overlap contributes significantly to sensitivity and reliability of the improved testing apparatus.

In a presently preferred embodiment of the apparatus, which is assumed to scan the external surface of a cigarette rod having a diameter close to or equaling 8 mm, the length of a section 28 or 28' (as considered in the circumferential direction of the carrier 22) can be approximately 4 mm and, if the focusing means comprises a total of eight systems 13, the extent of overlap 29 between each pair of neighboring sections 28, 28' can be a little less than 1 mm. The circumferential length of each of the diaphragms 23 in the carrier 22 is then in the range of 2 mm because the imaging ratio of the systems 13 is assumed to be two-to-one. Such dimensioning ensures that each of the sections 28, 28' is fully imaged onto the photosensitive surface of the respective transducer 14. The sensitivity of the testing apparatus is particularly pronounced due to the fact that the transducers 14 are secured directly to the carrier 22 immediately behind the respective diaphragms 23.

The outputs of the transducers 14 can transmit defect signals and other signals to any suitable evaluating circuit, e.g., a circuit of the type disclosed in commonly owned German Offenlegungsschrift No. 29 40 408.

It will be readily appreciated that the path of propagation of light which is reflected by the annular surfaces 27 of successive increments of the moving rod 3 is not exactly in the plane X—X, i.e., one cannot speak here of reflection of light into the plane X—X as the term "reflection" is used in optics in a classical sense. The consistency of the wrapper of the rod 3 is such that the incident light is dispersed, at least to a certain extent, in a number of different directions but the maximum reflection takes place into or close to the plane X—X. Therefore, the axes of the systems 13 of the focusing means are located in the plane X—X to ensure that the inner lenses 13" of such systems receive maximum amounts of reflected light.

As mentioned above, the transducers 14 can be simply glued to the external surface of the carrier 22 immediately behind the corresponding diaphragms 23. However, it is equally possible to secure the transducers 14 to the carrier 22 in any other suitable way without departing from the spirit of the invention. All that counts is to ensure that the diaphragms 23 as well as the photosensitive surfaces of the transducers 14 are located in or very close to the focal planes of the respective systems 13. In other words, it is desirable and advantageous to ensure that light which is reflected by successive annular surfaces 27 and impinges upon the optical systems 13 be accurately focused upon the corresponding photosensitive detectors 14.

The utilization of light emitting devices 11 and 12 which emit green light in the wavelength range of between 0.49 and $0.58\mu$ is evidently not limited to the scanning of a continuous rod, e.g., a rod of coherent cigarettes upstream of the cutoff which severs the rod at regular intervals so that the rod yields a file of discrete cigarettes of unit length of multiple unit length. A testing apparatus which employs devices for emission of green light in the wavelength range of between 0.49 and $0.58\mu$ can be used with advantage for the testing of discrete rod-shaped articles irrespective of whether the articles move axially or sideways (at right angles to their respective axes). Such light emitting devices (and transducers which are sensitive to light in the aforementioned range) can be used with advantage in many presently known testing apparatus as a superior substitute for heretofore employed light emitting devices and photosensitive detectors. The utilization of such light emitting devices and detectors enhances the versatility of testing apparatus because the apparatus can detect defects which were not detectable in apparatus employing sources of red or infrared light and corresponding transducers.

It was further found that testing apparatus employing sources of green light and appropriate detectors can be used with advantage for the testing of a continuous filter rod or of discrete sections of a subdivided filter rod. For example, if a testing apparatus employing sources of green light and corresponding transducers is used in a filter tipping machine to detect defective filter cigarettes (e.g., cigarettes which do not have any filter mouthpieces), reflection of green light by the white end face of a filter mouthpiece containing customary acetate fibers will induce the associated transducer to generate a signal which is indicative of a satisfactory filter cigarette. However, if green light is reflected by particles of tobacco (because the rod-shaped article which is being tested does not have a filter mouthpiece), the transducer which receives reflected light transmits a defect signal. Actually, the transducer then fails to receive any reflected light or does not receive a sufficient amount of reflected light so that it automatically generates a defect signal which is processed and used for segregation of the corresponding article from satisfactory filter cigarettes.

As described in connection with FIGS. 1 and 2, the testing apparatus (using devices 11 and 12 which emit green light and appropriate transducers 14) can be used for scanning the external surface of a continuous cigarette rod which is turned out by a cigarette rod making machine. In addition, the apparatus can be used to perform other types of testing operations. For example, if the apparatus is installed in a region where a file of discrete plain cigarettes, filter cigarettes, filter rod sections or the like advances along a predetermined course, it can be used to ascertain the width of the clearances or gaps between successive rod-shaped articles of the file. Determination of the width of such gaps is desirable and advantageous preparatory to conversion of the file into a row wherein the articles advance one after the other at right angles to their respective axes. If the width of the gaps is insufficient, a nextfollowing article is likely to interfere with the transfer of the preceding article from the course wherein the article was moved axially into the course wherein the article is supposed to advance at right angles to its axis. As a rule, the width of the gaps is between 3 and 5 mm. A testing apparatus operating with green light is capable of ascertaining the width of gaps between successive rod-shaped articles of a file even if the articles are transported at a high or extremely high speed such as necessary in a modern cigarette maker, filter tipping machine or the like. Heretofore, such gaps were monitored by testing apparatus with means for emitting red or infrared light. The presence of tobacco shreds or other fragments of tobacco leaves in the gaps was interpreted as the absence of a gap. On the other hand, a testing apparatus which employs means for emitting green light and appropriate transducers can generate satisfactory signals even if the gaps between neighboring articles of a file of rod-shaped articles are filled with tobacco particles, i.e., the improved apparatus is not "fooled" by the presence of fragments of tobacco leaves between successive rod-shaped articles of the tobacco processing industry.

Apparatus which monitor the gaps between successive articles of a file of rod-shaped articles of the tobacco processing industry are disclosed, for example, in commonly owned U.S. Pat. Nos. 4,025,770 and 4,147,173 to Reuland. The operation of such apparatus can be improved by using one or more devices which emit green light in the aforementioned range of wavelengths and by using one or more photosensitive detectors which react to such light.

Apparatus which can test the ends of filter cigarettes for the presence or absence of filter mouthpieces are disclosed, for example, in commonly owned allowed patent application Ser. No. 351,475 filed Feb. 23, 1982 by Buchegger et al. The utilization of sources of green light and appropriate detectors entails a pronounced improvement of the versatility and sensitivity of such apparatus.

Commonly owned copending patent application Ser. No. 620,578 filed June 14, 1984 by Heitmann discloses an apparatus which can test the external surfaces of discrete rod-shaped articles of the tobacco processing industry. The versatility and accuracy of such testing apparatus can be enhanced by installing therein one or more devices which emit green light within the aforementioned range of wavelengths and using them in conjunction with detectors which react to such light.

The resolution capability of the improved testing apparatus is surprisingly high. This is due, in part, to the fact that the axial length of the annular surfaces 27 equals or approximates the maximum dimension of the smallest defect which is to be detected by the apparatus. Thus, each and every defect which is to be detected (and whose detection normally leads to segregation of the corresponding cigarette from satisfactory cigarettes) invariably and fully influences the impingement of reflected light upon at least one of the transducers 14 so that such one transducer can generate an output signal which induces the evaluating circuit to record the presence of a defect and/or to effect segregation of the corresponding rod-shaped article.

The resolution capability of the improved apparatus is enhanced still further due to the aforediscussed distribution of focusing systems 13 and diaphragms 23 in such a way that the neighboring arcuate sections 28, 28' of successive annular surfaces 27 in the testing zone 9 partially overlap each other and the extent of overlap matches or approximates the maximum dimension of the smallest defect to be detected by the apparatus. Thus, and as already mentioned above, the resolution capability of the improved apparatus can be favorably influenced in a number of very simple but highly effective ways. Each and every defect which is sufficiently large or prominent to warrant segregation of the respective article from satisfactory articles is invariably detected in its entirety by at least one of the detectors 14, i.e., the sensitivity of the apparatus is high and the novel distribution of focusing means, diaphragms and detectors ensures that the apparatus can scan each and every portion of the external surface of the rod 3.

An additional important advantage of the improved apparatus is that, if it employs devices 11 and/or 12 which emit light in the wavelength range of 0.5 to $0.7\mu$, and especially in the range of 0.49 to $0.58\mu$, the external surface of the rod 3 is tested with visible light, i.e., with light which is also perceived by the manufacturer, purchaser or inspector of the ultimate products. In other words, testing with the improved apparatus closely resembles testing with the human eye except that it is more sensitive, more accurate and more reliable. Therefore, the apparatus can readily detect all such defects which would be detected by the manufacturer, purchaser or inspector and would be construed as defects which adversely influence the appearance and/or other desirable characteristics of cigarettes, filter rod sections and analogous products of the tobacco processing industry. The apparatus is particularly sensitive and reliable if the devices 11 and/or 12 emit green light in the wavelength range of between 0.49 and $0.58\mu$.

An additional important advantage of the improved apparatus is its simplicity. Such simplicity is particularly enhanced by the provision of a carrier 22 which is a metallic band that can be assembled of several arcuate sections and to which the detectors 14 are secured by adhesive or in any other suitable way. The installation and adjustment of a ring-shaped carrier are very simple and take up little time.

The operation of the improved testing apparatus can be enhanced still further if the focusing means comprises optical systems 13 or analogous systems of great focal length. This reduces the influence of eventual radial stray movements of the rod 3 upon the characteristics of signals which are generated by the outputs of the detectors 14. In many instances, the focal length of the optical systems which form part of the focusing means will depend upon the availability of space for installation of the apparatus in a cigarette rod making or other machine as well as on the desired degree of accuracy with which the rod 3 is to be tested for the presence or absence of defects in its external surface.

The utilization of visible light distinguishes the improved testing apparatus from heretofore known testing apparatus which normally operate with red or infrared light and, therefore, cannot test for the presence or absence of all such defects which are likely to be detected by the human eye. Moreover, the apparatus is simpler and more reliable as well as more sensitive and more versatile than heretofore known apparatus. For example, the feature that the illuminating means comprises or preferably comprises two groups of light emitting devices 11 and 12 which are disposed at the opposite sides of the plane X—X eliminates or greatly reduces the possiblity of development of shadows in the testing zone 9 and attendant undesirable influencing of signals which are generated by the photosensitive detectors. As explained above, illumination from one side of the plane X—X could result in the development of shadows due to the fact that the external surface of the rod 3 is often uneven and, while the unevennesses might not be readily detectable by the human eye, they cause the incident light to create shadows which are interpreted by the photosensitive detectors as defects and thus distort the results of the measurements. The absence of shadows ensures that the number of unnecessary rejects is reduced to zero or to a fraction of rejects in conventional apparatus.

The positions of the diaphragms 23 with reference to the associated optical systems 13 can be selected and adjusted with a very high degree of accuracy. All that is necessary is to shift the carrier 22 relative to the external surface of the cylindrical portion of the adapter 18 in the axial and/or in the circumferential direction. Moreover, the carrier 22 can be machined with a very high degree of accuracy so that the distribution of its diaphragms 23 matches exactly the distribution of sleeves 16 in the holder 17.

The versatility of the improved apparatus is especially high if the devices 11 and/or 12 emit green light within the aforediscussed range of wavelengths. This enables the apparatus to detect defects (e.g., spots or specks of oil or other fatty substances) which can be detected by the human eye but not by appratus using infrared light. At any rate, apparatus using infrared light cannot detect spots of oil or the like with the same degree of reliability and predictability as the improved apparatus if the devices 11 and/or 12 are sources of green light within the aforementioned range of wavelengths. The utilization of sources of green light also brings about further important advantages. Thus, the nature of a testing operation is often such that incident light is not invariably reflected by white surfaces, e.g., by the end faces of filter mouthpieces which are made of acetate fibers and/or by white cigarette paper. For example, and as already mentioned above, it happens quite frequently that incident light is reflected by fragments of tobacco leaves. If the incident light is infrared light, it is strongly reflected by fragments of tobacco and this can result in misleading measurements, e.g., if tobacco particles penetrate into the gaps between successive cigarettes of a file of cigarettes and the testing apparatus is to ascertain the width of such gaps. Therefore, the provision of light sources which emit green light and cooperate with appropriate photosensitive detectors in apparatus for testing continuous rods or discrete sections of rods by itself constitutes a novel and meritorious feature of the present invention. As mentioned above, testing apparatus employing such light sources and detectors can test rod-shaped material of the tobacco processing industry in a manner which is analogous to but more accurate, more sensitive and more predictable than visual testing by purchasers, inspectors and/or other interested persons. The improved apparatus which use one or more sources of green light in appropriate wavelength ranges and corresponding detectors can be readily designed to exhibit a sensitivity which matches that of the human eye. Thus, the apparatus can be designed to detect defects which would be detected, for example, by the purchaser of cigarettes but to disregard all other defects which would not deter a smoker from purchasing the product. Otherwise stated, the apparatus can be designed to test continuous rods and/or discrete rod-shaped articles with a view to ensure detection and segregation of those articles only which would be objectionable to the manufacturer, purchaser, inspector or another interested person but to disregard all other defects (if any) which would not irritate such persons and would not detract from the appearance and/or quality of the ultimate products. This is in contrast to the testing with infrared light which induces the detector means to generate defect signals in response to detection of flaws which are not detectable by the human eye and merely lead to segregation of articles which would be acceptable to the purchaser.

The utilization of light emitting devices in the form of diodes is desirable and advantageous in many instances, for example, when it is necessary to construct and assemble a very compact testing apparatus because there is little room for installation of such apparatus in a cigarette rod making, filter tipping or like machine. Moreover, such light emitting devices generate negligible amounts of heat energy.

Figure 3:
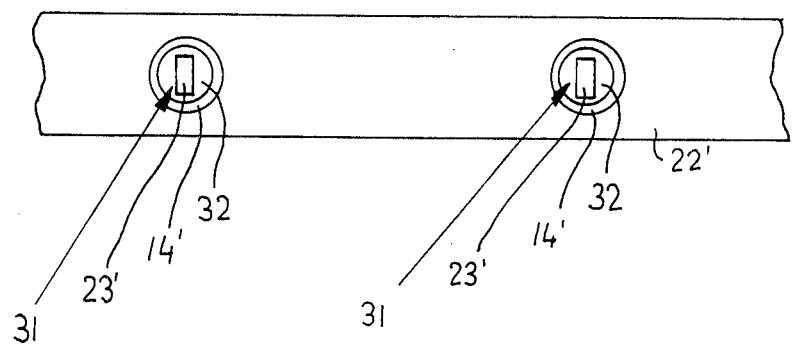
FIG. 3 is a fragmentary developed view of a modified carrier of diaphragms which can be used in the improved testing apparatus.

FIG. 3 shows a portion of a modified testing apparatus, namely a portion of a ring-shaped carrier 22' for diaphragms and light-sensitive detectors 14' (e.g., photosensitive transducers) which can be used in the apparatus of FIGS. 1 and 2 in lieu of the carrier 22. Each detector 14' can constitute a commercially available article and has a photosensitive surface 31 facing toward the corresponding system 13 of lenses 13' and 13" (not shown). The detectors 14' (of which only two are shown in FIG. 3) are equidistant from each other, as considered in the circumferential direction of the carrier 22', and each detector receives reflected light from a discrete system of lenses.

Each detector 14' can be adhesively secured to the inner side of the ring-shaped carrier 22', inserted into an opening of the carrier or otherwise affixed thereto. Each photosensitive surface 31 carries a layer or coating 32 of opaque material which adheres to the respective detector 14' and constitutes a diaphragm. To this end, each layer 32 defines an elongated rectangular slit 23' which permits reflected light (e.g., green light emitted by a diode and reflected by the arcuate section 28 or 28' of the annular surface 27 at the testing station) to reach the photosensitive surface 31 of the corresponding detector 14'.

The carrier 22 or 22' can be omitted if the detectors 14 or 14' are otherwise mounted on the support 1 in such a way that they receive reflected light which is focused by the respective system of optical elements. All that counts is to ensure that the systems 13 or analogous systems of great focal length can adequately focus reflected light (if any) upon the slits 23 or 23' and the adjacent detectors 14 or 14'.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Apparatus for scanning the external surface of a moving rod-shaped product of the tobacco processing industry for the presence or absence of defects, especially for scanning the circumferentially complete annular external surfaces of a series of coaxial cigarettes, comprising guide means defining a predetermined course along which the product moves axially; a support surrounding a portion of said course; illuminating means including at least one ring-shaped group of light emitting devices carried by said support and arranged to direct light against the external surfaces of successive increments of the product so that such external surfaces reflect light into a predetermined plane; an annulus of diaphragms spacedly surrounding said course and being disposed in the path of propagation of light which is reflected into said plane; means for focusing reflected light upon said diaphragms, comprising optical elements each arranged to focus light which is reflected by arcuate sections of annular surfaces of successive increments of the product; and a light-sensitive detector disposed immediately behind each of said diaphragms, as considered in the direction of propagation of reflected light, to be exposed to light passing through the respective diaphragm and reflected by predetermined portions of the annular surfaces of successive increments of the product.

2. The apparatus of claim 1, wherein said plane is at least substantially normal to said course and said illuminating means includes two groups of light emitting devices, said groups being disposed at the opposite sides of said plane and the light emitting devices of each of said groups being arranged to direct light at an oblique angle to said course and into the region where said plane intersects said course.

3. The apparatus of claim 2, wherein each of said diaphragms is a slit diaphragm and further comprising a ring-shaped carrier for said diaphragms, said carrier being mounted on said support and said detectors including transducers mounted on said carrier.

4. The apparatus of claim 3, wherein said slit-shaped diaphragms extend in the circumferential direction of said carrier.

5. The apparatus of claim 4, wherein said diaphragms are equidistant from one another, as considered in the circumferential direction of said carrier.

6. The apparatus of claim 1, wherein each of said sections has a substantially rectangular outline.

7. The apparatus of claim 1, wherein the ratio of the areas of said arcuate sections to the areas of slits in the respective diaphragms is or approximates two-to-one.

8. The apparatus of claim 1, wherein the width of said annular surfaces, as considered in the longitudinal direction of said course, equals or approximates the maximum dimension of the smallest defect which is to be detected by the apparatus.

9. The apparatus of claim 1, wherein the distribution of said optical elements around said course is such that the neighboring arcuate sections overlap each other, as considered in the circumferential direction of said carrier.

10. The apparatus of claim 9, wherein the extent of overlap of neighboring arcuate sections equals or approximates the maximum dimension of the smallest defect which is to be detected by the apparatus.

11. The apparatus of claim 1, wherein each of said light emitting devices is arranged to emit light in the wavelength range of between 0.5 and $0.7\mu$.

12. The apparatus of claim 11, wherein said range is between 0.49 and $0.58\mu$.

13. The apparatus of claim 1, further comprising a ring-shaped carrier for said diaphragms, said carrier being mounted on said support and said detectors being adhesively secured to said carrier.

14. The apparatus of claim 1, further comprising a multi-piece ring-shaped carrier for said diaphragms, said carrier being mounted on said support.

15. The apparatus of claim 1, further comprising a ring spacedly and concentrically surrounding said course, said ring being mounted on said support and having an annulus of slits each of which constitutes one of said diaphragms.

16. The apparatus of claim 1, wherein said focusing means includes a system of lenses of great focal length for each of said diaphragms.

17. The apparatus of claim 1, wherein each of said detectors has a light-sensitive surface and each of said diaphragms includes a layer of opaque material applied to the respective light-sensitive surface and defining a slit for the passage of reflected light to the respective light-sensitive surface.

18. The apparatus of claim 17, further comprising a ring-shaped carrier for said detectors, said carrier being mounted on said support and spacedly surrounding said course.

19. The apparatus of claim 1, wherein each of said light emitting devices is arranged to emit green light.

20. The apparatus of claim 19, wherein each of said light emitting devices includes a diode.

21. Apparatus for scanning the external surface of a moving rod-shaped product of the tobacco processing industry for the presence or absence of defects, especially for scanning the external surfaces of a series of coherent or discrete cigarettes, comprising means for illuminating successive increments of the external surface of a moving product so that such increments reflect the incident light, said illuminating means being arranged to emit green light in the wavelength range of between 0.49 and $0.58\mu$; and light-sensitive detector means disposed in the path of propagation of light which is reflected by successive increments, said detector means being sensitive to light within said range of wavelengths.

22. The apparatus of claim 21, wherein said illuminating means includes a plurality of green light emitting diodes.

* * * * *